US012778702B2

(12) United States Patent
Frischauf et al.

(10) Patent No.: US 12,778,702 B2
(45) Date of Patent: Nov. 3, 2026

(54) DEVICE FOR DESTROYING CELL STRUCTURES WITHOUT DAMAGING THEIR SURROUNDINGS

(71) Applicant: SIGMA-7 E.U., Zwölfaxing (AT)

(72) Inventors: Norbert Frischauf, Zwölfaxing (AT); Alexander Kraus, Vienna (AT); Robert Mayer, Vienna (AT)

(73) Assignee: SIGMA-7 E.U., Zwölfaxing (AT)

( * ) Notice: Subject to any disclaimer, the term of this patent is extended or adjusted under 35 U.S.C. 154(b) by 765 days.

(21) Appl. No.: 18/248,963

(22) PCT Filed: Oct. 15, 2021

(86) PCT No.: PCT/AT2021/060377

§ 371 (c)(1),
(2) Date: Apr. 13, 2023

(87) PCT Pub. No.: WO2022/077045

PCT Pub. Date: Apr. 21, 2022

(65) Prior Publication Data

US 2023/0380922 A1 Nov. 30, 2023

(30) Foreign Application Priority Data

Oct. 15, 2020 (AT) .............................. A 50886/2020

(51) Int. Cl.
*A61B 34/00* (2016.01)
*A61K 41/00* (2020.01)
(Continued)

(52) U.S. Cl.
CPC .............. *A61B 34/73* (2016.02); *A61K 41/00* (2013.01); *A61N 2/004* (2013.01); *A61N 2/02* (2013.01);
(Continued)

(58) Field of Classification Search
CPC .. A61B 34/73; A61B 2034/733; A61K 41/00; A61N 2/004; A61N 2/02; H01F 7/202
See application file for complete search history.

(56) References Cited

U.S. PATENT DOCUMENTS

2013/0172728 A1* 7/2013 Gaitas .................. A61M 5/007 600/12

FOREIGN PATENT DOCUMENTS

AT 508394 B1 * 12/2011 ......... G01N 33/5005

OTHER PUBLICATIONS

English Translation AT-508394 B1 (Year: 2011).*
International Search Report and Written Opinion, mailed Jan. 28, 2028, from PCT/AT2021/060377.

* cited by examiner

*Primary Examiner* — Carrie R Dorna
*Assistant Examiner* — Joshua Daryl D Lannu
(74) *Attorney, Agent, or Firm* — Workman Nydegger

(57) ABSTRACT

A device for environmentally friendly destruction of health-relevant and cosmetically/aesthetically relevant cell structures, in particular tumour cells, which have at least one metallic nanoparticle on their cell membrane, is disclosed. The device includes a primary coil for generating an inhomogeneous primary magnetic field, a secondary coil for generating an inhomogeneous secondary magnetic field and a control device which is designed for actuating the primary coil in such a way that the nanoparticle is deflected by the primary magnetic field and for actuating the secondary coil in such a way that the secondary magnetic field oscillates in relation to the primary magnetic field and deforms it periodically in order to generate Alfvén waves which deflect the nanoparticle, whereby the cell membrane of the cell structure is torn up by the nanoparticle and the cell structure is consequently destroyed.

8 Claims, 2 Drawing Sheets

Figure 1A:
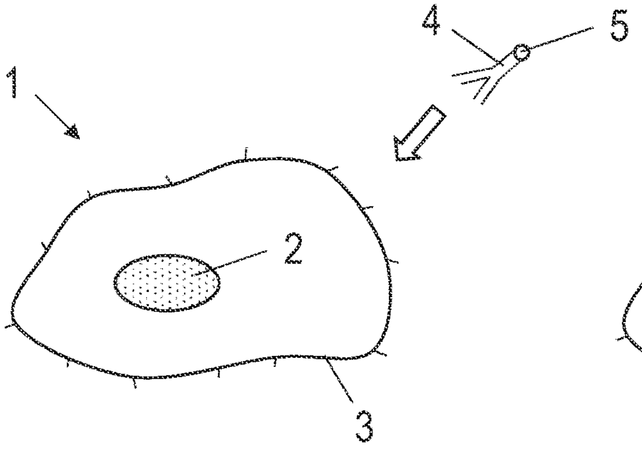

(51) Int. Cl.
*A61N 2/00* (2006.01)
*A61N 2/02* (2006.01)
*H01F 7/20* (2006.01)

(52) U.S. Cl.
CPC ........ *H01F 7/202* (2013.01); *A61B 2034/733* (2016.02)

DEVICE FOR DESTROYING CELL STRUCTURES WITHOUT DAMAGING THEIR SURROUNDINGS

The present invention relates to a device for the specific environmentally friendly destruction of health-relevant and cosmetically/aesthetically relevant cell structures, in particular tumour cells, which have at least one metallic nanoparticle on their cell membrane.

A major problem in the treatment of cancer is the selective access and controlled destruction of the tumour cells in the patient's body. After the surgical removal of tumours, individual tumour cells often remain in the body, from which new tumours may develop. A controlled destruction of those tumour cells is often not possible with a classic follow-up treatment using chemotherapy and radiation. Furthermore, the destruction of healthy cells puts an additional burden on the patient.

In order to overcome those disadvantages, e.g. the so-called NanoTherm therapy is known from the prior art, in which nanoparticles containing iron oxide are introduced directly into the tumour in a biopsy-like procedure at baseline in order to set them into vibration afterwards with alternating magnetic fields. The primary mechanism of action of this process is based on thermally damaging the tumour. As a result of the heat input, the tumour cells are either made to burst directly, or they are driven to cell suicide (apoptosis). Since it is relatively difficult to precisely control the heat dissipation and since the heat input persists for some time even after the alternating magnetic field has been deactivated, there is a certain vagueness in the effect and surrounding healthy tissue runs the risk of being damaged.

From other fields of technology—as described, for example, in AT 508 394 B1 for non-therapeutic applications—it is known that antibodies doped with nanoparticles can be selectively docked to the cell membrane. In order to rupture the cell membrane, thus destroying the cell, the nanoparticles are deflected to a sufficient degree, which is achieved using a simple coil. For this purpose, the coil generates an alternating magnetic field to set the nanoparticles into a simple vibration, which, in some cases, is sufficient to damage the cell membrane. However, it has been shown that such devices exhibit an efficiency which is too low particularly for the destruction of tumour cells and, furthermore, require long treatment times.

It is therefore the object of the invention to provide a device for the specific environmentally friendly destruction of health-relevant and cosmetically/aesthetically relevant cell structures, in particular tumour cells, which overcomes the disadvantages of the prior art.

According to the invention, this is achieved by a device for the specific environmentally friendly destruction of health-relevant and cosmetically/aesthetically relevant cell structures, in particular tumour cells, which have at least one metallic nanoparticle on their cell membrane, the device comprising a primary coil for generating an inhomogeneous primary magnetic field, a secondary coil for generating an inhomogeneous secondary magnetic field and a control device which is designed for actuating the primary coil in such a way that the nanoparticle is deflected by the primary magnetic field and for actuating the secondary coil in such a way that the secondary magnetic field oscillates in relation to the primary magnetic field and deforms it periodically in order to generate Alfvén waves which deflect the nanoparticle, whereby the cell membrane of the cell structure is torn up by the nanoparticle and the cell structure is consequently destroyed.

The device according to the invention has the advantage that the Alfvén waves generated by two coils, in contrast to simple alternating magnetic fields, allow a particularly effective destruction of the cell structures, since the nanoparticles can be deflected to a greater extent by the Alfvén waves and do not oscillate around a rest position.

In order to use the device according to the invention, the nanoparticles are preliminarily attached to the cell membrane in a known manner, e.g., by introducing specially doped antibodies into the body in the vicinity of the tumour. Due to the selective attachment mechanism, the antibody couples to the tumour cell and healthy cells are largely spared. The activation of the primary magnetic field leads to coupling with the metallic nanoparticles, in this case iron nanospheres, with which the antibodies have been doped. If the secondary magnetic field is now activated, the primary magnetic field is disturbed. The displacement of the latter manifests itself through coupling with the iron nanosphere in such a way that the entire antibody is abruptly accelerated. In the case of the device according to the invention, the force acting on the iron nanospheres or, respectively, on the antibody is dimensioned such that the cell membrane is destroyed, whereby the tumour cell is irreversibly damaged.

In the course of the development of the invention, it has been shown that not only tumour cells, i.e., health-relevant cell structures, but also cosmetically/aesthetically relevant cell structures can be destroyed with the method according to the invention. In this case, this is understood to include pigment deposits in age spots and liver spots, colour pigments in tattoos and/or port-wine stains or also warts, elevations (e.g., naveus) and/or scar tissue.

The physical basis of the Alfvén waves was already described in 1942 by the subsequent Swedish Nobel Prize winner Hannes Alfvén. In this connection, the disruption of a magnetic field (in the case of the present invention, the displacement of the primary magnetic field by the secondary magnetic field) creates a force acting on magnetically conductive materials that are in the immediate vicinity. It has already been possible to utilize the technical implementation of the generation of Alfvén waves for specific applications in which, however, plasma always located on the inner circumference of the coils is accelerated in order to, for example, generate an ion beam for selective treatment or achieve a drive. Hence, in these applications—in contrast to the device according to the invention—plasma is always emitted from the device, for which reason they cannot be utilized for cell walls doped with nanoparticles, as they do not permit environmentally friendly usage.

In a preferred embodiment, the control device is designed for actuating the primary coil in a temporally constant manner and for actuating the secondary coil with a change over time. The temporally constant actuation of the primary coil would thus create a primary magnetic field which would be temporally constant without the influence of the secondary magnetic field. In this embodiment, it is thus only the secondary magnetic field that provides the dynamic aspects for the generation of the Alfvén waves. Alternatively, embodiments are also possible in which both the primary coil and the secondary coil can be actuated in a time-varying manner in order to generate the Alfvén waves, wherein, however, the control of the coils becomes more complicated, in contrast to the preferred embodiment.

The primary coil and the secondary coil are preferably toroidal coils that are arranged essentially concentrically, which significantly simplifies the structure of the device according to the invention. Furthermore, the toroidal coils advantageously have the same diameter and the same windings, wherein it is possible to deviate from these specifications.

With the device according to the invention, it is possible for treatments to destroy cell structures doped with metallic nanoparticles to be carried out faster than in the prior art. Therefore, the control device is advantageously designed for actuating the primary coil and the secondary coil in the above-mentioned manner over a period of up to a few minutes, e.g., 10 to 180 seconds (preferably over a period of essentially 30 seconds). Alternatively, for example, a period of 60 to 180 seconds can be provided. After a certain time, the proportion of destroyed cell structures already drops to a level at which any further treatment does not have too great an effect, since the major part of the cell structures has already been destroyed so that, after several minutes, no further cell structures are actually destroyed. However, for solutions from the prior art involving only one magnetic coil, the above-mentioned periods of time would be too short to destroy a comparable proportion of cell structures.

Moreover, the device according to the invention allows particularly small configurations, for which reason the primary coil and the secondary coil are preferably installed in a handheld device. Handheld devices are understood to be devices with housings which, for example, have a volume of less than 0.5 $m^3$, preferably less than 0.001 $m^3$. In this case, the handheld device can advantageously be designed in the size of an ultrasonic probe so that similarly simple operability can also be achieved with the device according to the invention.

The control unit can thus be arranged, for example, in a computer connected to the handheld device, with the computer being connected to the handheld device via a cable or a wireless interface. Alternatively, the control unit can also be installed in the handheld device, which constitutes a particularly advantageous embodiment since a completely self-sufficient device is created, which is particularly suitable for use in treatments during home visits.

The control unit is preferably designed for adjusting the efficiency of the device by selecting the duration of the actuation and/or by selecting the strength of the primary magnetic field and/or the secondary magnetic field. This is advantageous particularly if, as a result of an excessively high degree of efficiency as could be achieved by the device according to the invention, the amount of destroyed oncological tissue would lie above a threshold at which sepsis, blood poisoning or another health risk might occur.

Advantageous and non-limiting embodiments of the invention are explained in further detail below with reference to the drawings.

FIGS. 1*a*-1*d* show the selective destruction of cell structures with the device according to the invention.

Figure 2:
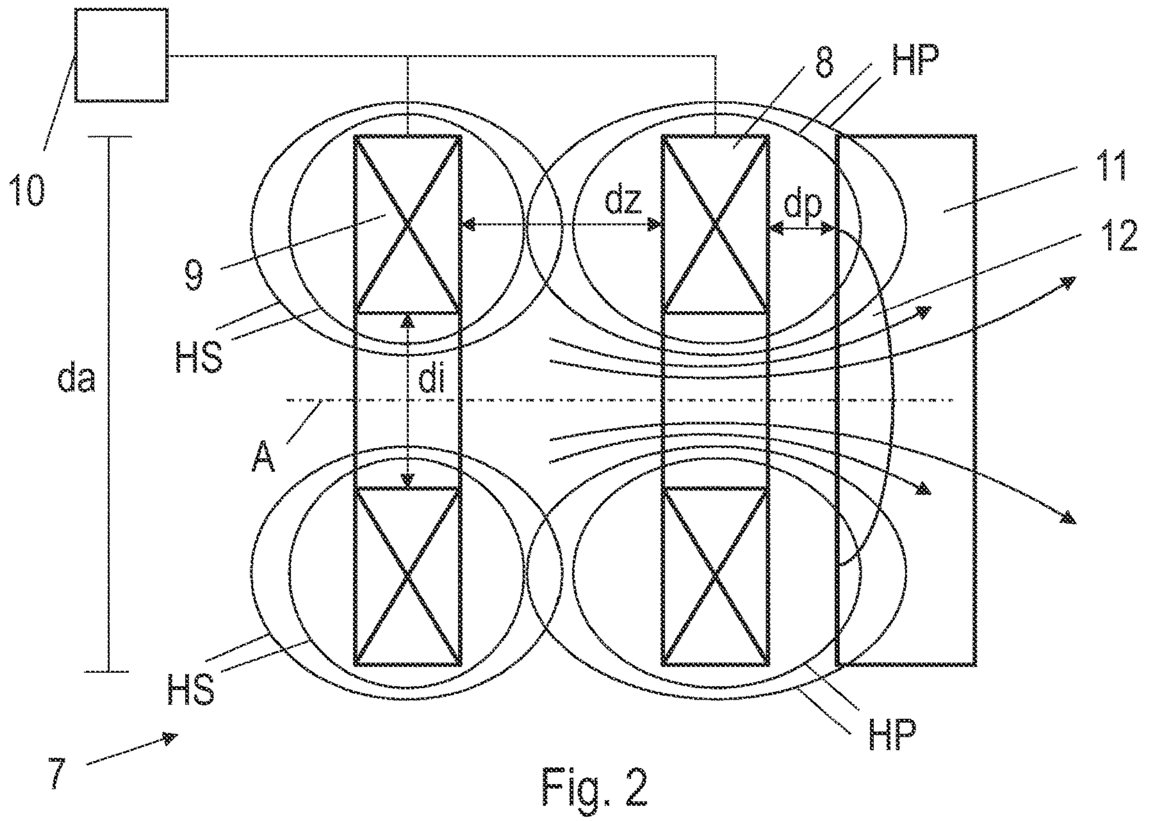

FIG. 2 shows the device according to the invention with a primary coil and a secondary coil.

Figure 3A:
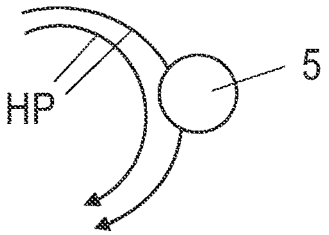
Figure 3B:
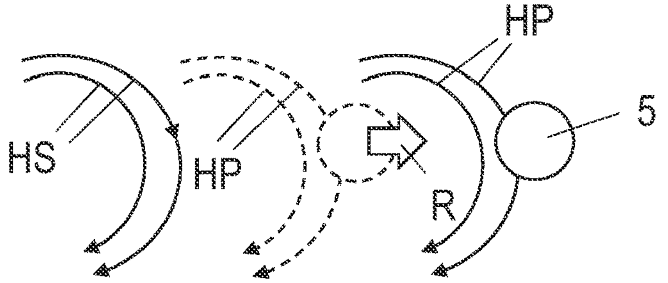

FIGS. 3*a* and 3*b* show in detail the generation of Alfvén waves by a primary magnetic field and a secondary magnetic field.

FIG. 1*a* shows a cell, e.g., a tumour cell or cancer cell 1 comprising a cell nucleus 2 and a cell membrane 3, which is located in a tissue near the surface of a human or animal body. Such tumour cells 1 are usually located in the vicinity of healthy cells that should not be damaged during a treatment process. For this purpose, antibodies 4 attaching themselves only to selected tumour cells 1, but not to healthy cells, are used in a known manner. In this case, the antibodies 4 are doped with at least one metallic nanoparticle 5, which generally contains iron oxide and/or is designed as an iron nanosphere.

The method is described for a tumour cell 1 on the basis of the figures, although the method could also be performed for other health-relevant cell structures or even for cosmetically/aesthetically relevant cell structures such as pigment deposits in age spots and liver spots, colour pigments in tattoos and/or port-wine stains or also warts, elevations (e.g., naveus) and/or scar tissue. If reference is made below to a tumour cell 1, the method can thus be performed equally also for another one of the aforementioned cell structures.

Figure 1B:
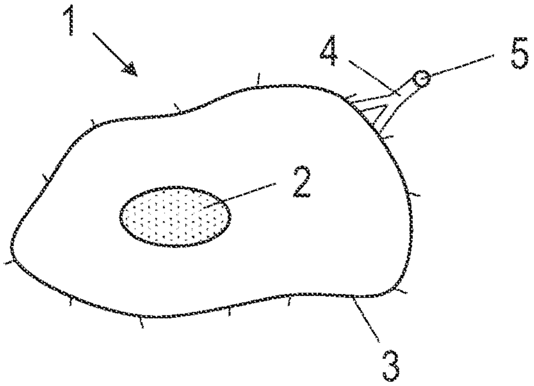

FIG. 1*b* shows the tumour cell 1 in a state in which the antibody 4 adheres to the cell membrane 3. In practice, several doped antibodies 4 can dock onto the tumour cell 1, which further enhances the mode of action of the device described below. The bond between the cell membrane 3 and the antibody 4 is so strong that the antibody 4 cannot detach from the cell membrane 3 without tearing it up. However, since a tumour cell 1 with a ruptured cell membrane 3 is not viable, rupturing the cell membrane 3 is equivalent to destroying the tumour cell 1.

Figure 1C:
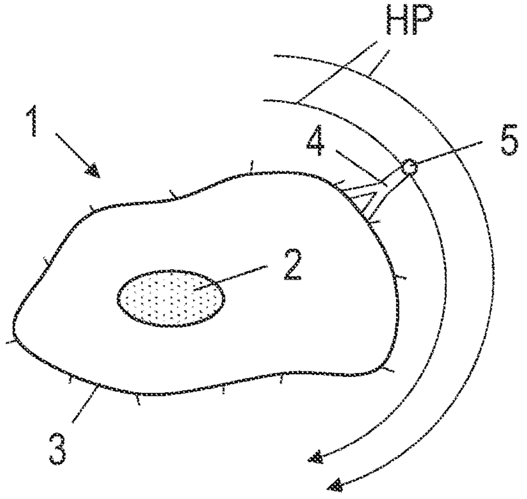

In order to rupture the cell membrane 3, as shown in FIG. 1*c*, an inhomogeneous primary magnetic field HP is applied in the area of the tumour cell 1, which induces an opposing field into the nanoparticle 5, i.e., the nanoparticle 5 is coupled to the primary magnetic field HP.

Figure 1D:
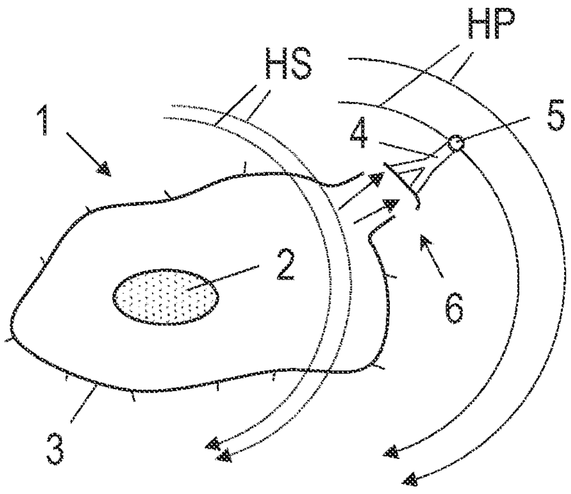

As illustrated in FIG. 1*d*, the cell membrane 3 is torn up by an Alfvén wave deflecting the nanoparticle 5. For this purpose, a secondary magnetic field HS is applied in the area of the primary magnetic field HP, which "displaces" the latter, whereby the Alfvén wave arises. Said wave is strong enough for tearing the nanoparticle 5 from the cell membrane 3, creating a fracture 6 therein, as will be explained in detail below with reference to FIGS. 3*a* and 3*b*.

FIG. 2 shows a device 7 that is suitable for the environmentally friendly destruction of tumour cells which have at least one metallic nanoparticle 5 on their cell membrane 3. As is known to those skilled in the art, environmentally friendly means in this context that healthy cells are affected as little as possible during treatment with the device 7.

The device 7 comprises a primary coil 8 for generating the inhomogeneous primary magnetic field HP, a secondary coil 9 for generating the inhomogeneous secondary magnetic field HS and a control device 10. For example, the primary and secondary coils 8, 9 are designed as toroidal coils with iron cores and each with a predetermined number of windings through which current is passed in a known manner in order to generate the respective magnetic fields HP, HS. In this case, the coils 8, 9 are usually arranged concentrically around an axis A.

The coils 8, 9 have an inner diameter di and an outer diameter da, with no guide tube, e.g. for plasma, being guided through the inner diameter di. The coils 8, 9 are arranged with a distance dz between each other. For application, the device 7 is positioned such that the primary coil 8 is at a positioning distance dp from a tissue 11 to be treated and the secondary coil 9 is arranged on the side of the primary coil 8 facing away from the tissue 11. In this arrangement, the device 7 allows the tissue 11 to be treated on a treatment area 12 which is located essentially symmetrically about the axis A. With the device 7 in the configuration as illustrated, treatment areas 12 close to the surface can be treated, whereby increased penetration depths can also be achieved by appropriately selecting the magnetic fields in order to also treat deeper-lying types of cancer.

The control device 10 is designed for actuating the primary coil 8 and the secondary coil 9. For example, the control device 10 can control the amperage of the current flowing through the windings of the coils 8, 9 in order to generate the magnetic fields HP, HS. It shall be understood that the control device 10 can control the primary coil 8 and the secondary coil 9 independently in order to generate the Alfvén waves.

The control device 10 can be designed in any way, for example, as an analog or digital control unit, e.g., as a computer. The power supply to the coils 8, 9, which is regulated by the control device 10, can be accomplished, for example, by an external power source or even by a battery. In addition, the control unit 10 can be connected to a data logger or have an external interface in order to record past operating times or possible sources of error.

According to FIG. 3*a*, in a first operating state, only the primary magnetic field HP is applied to the nanoparticle 5, i.e., the control device 10 actuates only the primary coil 8. The secondary coil 9, on the other hand, is not actuated. The primary magnetic field HP thus generates an opposing magnetic field within the nanoparticle 5.

In order to move the nanoparticle 5, the control device 10 also actuates the secondary coil 9 so that it generates the secondary magnetic field HS, which displaces the primary magnetic field HP, which is shown schematically in FIG. 3*b* by way of a transformation of the dashed representation of the primary magnetic field HP to the solid representation of the primary magnetic field HP. In this embodiment, the primary coil 8 is actuated in a temporally constant manner.

The control device 10 is designed for actuating the secondary coil 9 in such a way that the secondary magnetic field HS oscillates in relation to the primary magnetic field HP and deforms it periodically, i.e., after the second operating state of FIG. 3*b* has been reached, the first operating state of FIG. 3*a* is again adopted, then the second operating state of FIG. 3*b*, etc. This actuation enables via the oscillating secondary field HS that Alfvén waves are generated, which in turn deflect the nanoparticle 5. As shown in FIG. 3*b*, the Alfvén waves propagate linearly along the direction R so that the nanoparticle 5 is transported linearly in the direction R and does not oscillate around a rest position with a coil and an alternating field, as in the prior art.

However, other actuations by means of which Alfvén waves can be generated are possible, too. For example, the primary coil 8 can also be actuated in a time-varying manner so that the first primary magnetic field HP already oscillates before the secondary magnetic field takes effect. Furthermore, it is possible that the secondary magnetic field HS in the first operating state is reduced to a constant field intensity, rather than to zero.

By means of the Alfvén wave deflecting the nanoparticle 5, treatments for destroying the tumour cell 1 can be used which are significantly shorter than those known from the prior art. Possible treatment lengths with the device 7 according to the invention are, for example, 10-60 seconds. In order to achieve this, the control device 10 actuates the primary coil 8 and the secondary coil 9 in the above-mentioned manner over a maximum period of 60 seconds or even over a period of essentially 10 seconds.

Due to its compact design, the present device 7 is particularly suitable for mobile uses, since the coils 8, 9 shown in FIG. 2 can be compactly installed in a handheld device, for example, in the size of an ultrasonic probe as it is used for applications in soft-tissue examinations, in gynaecology or in case of muscle injuries. The control unit 10 can thus be installed compactly in the same handheld device or can be arranged externally, e.g., in the above-mentioned computer, which in turn can be connected to the handheld device with a cable or wirelessly.

Furthermore, the efficiency of the treatment can be selected precisely with the device 7, either via the duration of the treatment or via the selection of the strength of the magnetic field. This can be necessary in particular if, as a result of an excessively high degree of efficiency of the device 7, the amount of destroyed oncological tissue is above a threshold above which a health risk, e.g., sepsis or blood poisoning, might occur. However, depending on the treatment, this can be avoided, for example, if tumour cells 1 remaining after surgical tumour removal are destroyed with the device 7.

The invention claimed is:

1. A device for environmentally friendly destruction of health-relevant and cosmetically/aesthetically relevant cell structures, including tumour cells, each cell structure having at least one metallic nanoparticle attached to a respective cell membrane, the device comprising:

a primary coil for generating an inhomogeneous primary magnetic field, a secondary coil for generating an inhomogeneous secondary magnetic field, and a control device configured to:

actuate the primary coil to deflect the at least one metallic nanoparticle attached to the cell membrane of the cell structure by the primary magnetic field; and actuate the secondary coil such that the secondary magnetic field oscillates in relation to the primary magnetic field and deforms the primary magnetic field periodically to generate Alfvén waves, wherein the generated Alfven waves cause a displacement of the at least one metallic nanoparticle along a propagation direction such that the at least one metallic nanoparticle tears the cell membrane of the cell structure, thereby destroying the cell structure.

2. The device according to claim 1, wherein the control device is configured to actuate the primary coil in a temporally constant manner and to actuate the secondary coil with a time-varying signal to generate the Alfvén waves.

3. The device according to claim 1, wherein the primary coil and the secondary coil are toroidal coils, wherein the toroidal coils are arranged concentrically about a common axis and spaced to produce inhomogeneous fields.

4. The device according to claim 1, wherein the control device is configured to actuate the primary coil and the secondary coil for a duration of 10 to 180 seconds to generate the Alfven waves that mechanically rupture the cell membrane.

5. The device according to claim 1, wherein the primary coil and the secondary coil are integrated into a handheld device such that the primary coil and the secondary coil can be placed adjacent a treatment site.

6. The device according to claim 5, wherein the control device is integrated within the handheld device.

7. The device according to claim 1, wherein the control device is configured to adjust an efficiency of the device by controlling at least one of: a duration of actuation, an amplitude of the primary magnetic field, an amplitude of the secondary magnetic field in order to control a magnitude of nanoparticle displacement produced by the Alfven waves.

8. The device according to claim 1, wherein the displacement along the propagation direction is non-oscillatory.

* * * * *